(12) United States Patent
Jouanique-Dubuis et al.

(10) Patent No.: US 9,855,007 B2
(45) Date of Patent: Jan. 2, 2018

(54) METHOD AND SYSTEM FOR DETERMINING A VENTILATORY THRESHOLD

(71) Applicant: IEE INTERNATIONAL ELECTRONICS & ENGINEERING S.A., Echternach (LU)

(72) Inventors: Cecile Jouanique-Dubuis, Evrage (FR); Thomas Stifter, Trier (DE); Mathieu Lu-Dac, Luxembourg (LU); Franck Lemoine, Launstroff (FR); Christian Bour, Domprix (FR)

(73) Assignee: IEE International Electronics & Engineering S.A., Echternach (LU)

( * ) Notice: Subject to any disclaimer, the term of this patent is extended or adjusted under 35 U.S.C. 154(b) by 258 days.

(21) Appl. No.: 14/648,219

(22) PCT Filed: Nov. 27, 2013

(86) PCT No.: PCT/EP2013/074905
§ 371 (c)(1),
(2) Date: May 28, 2015

(87) PCT Pub. No.: WO2014/083079
PCT Pub. Date: Jun. 5, 2014

(65) Prior Publication Data
US 2015/0297133 A1 Oct. 22, 2015

(30) Foreign Application Priority Data
Nov. 28, 2012 (LU) .......................................... 92104

(51) Int. Cl.
*A61B 5/08* (2006.01)
*A61B 5/00* (2006.01)
(Continued)

(52) U.S. Cl.
CPC .......... *A61B 5/4866* (2013.01); *A61B 5/0205* (2013.01); *A61B 5/083* (2013.01);
(Continued)

(58) Field of Classification Search
USPC ........................................................ 600/484
See application file for complete search history.

(56) References Cited

U.S. PATENT DOCUMENTS

| | | | | |
|---|---|---|---|---|
| 3,659,590 | A * | 5/1972 | Jones | A61B 5/0803 600/538 |
| 6,174,289 | B1 * | 1/2001 | Binder | A61B 5/083 422/83 |
| 2010/0179438 | A1 * | 7/2010 | Heneghan | A61B 5/0205 600/484 |

FOREIGN PATENT DOCUMENTS

| | | | |
|---|---|---|---|
| DE | 10248500 A1 | * | 5/2004 |
| DE | 10248500 A1 | | 5/2004 |

OTHER PUBLICATIONS

Bisi, Maria Cristina, Rita Stagni, and Gianni Gnudi. "Automatic detection of maximal oxygen uptake and ventilatory threshold." Computers in biology and medicine 41.1 (2011): 18-23 (Bisi).*

(Continued)

*Primary Examiner* — Christian Jang
*Assistant Examiner* — Mitchell E Alter
(74) *Attorney, Agent, or Firm* — Reising Ethington P.C.

(57) ABSTRACT

A method of determining the ventilatory threshold of a subject in real time during an exercise session wherein data relating to physiological parameters of said subject are acquired and stored in function of time during the exercise session, said data including at least data indicative of the respiration and of the heart beat rate. The method includes a VT determination routine comprising the steps of: a) computing a first value of ventilatory threshold according to a first approach based on data relating to at least one of the (Continued)

physiological parameters acquired for the exercise session; b) computing a second value of ventilatory threshold according to a different, second approach based on data relating to at least one of the physiological parameters acquired for the exercise session; c) determining a confidence index for each of said first and second values of ventilatory threshold, wherein said confidence index reflects at least one of the detectability of the ventilatory threshold and the matching between the value of ventilatory threshold according to one approach and that according to the other approach.

26 Claims, 7 Drawing Sheets

(51) Int. Cl.
| | | |
|---|---|---|
| A61B 5/0205 | (2006.01) | |
| A61B 5/083 | (2006.01) | |
| A61B 5/0245 | (2006.01) | |
| A61B 5/0408 | (2006.01) | |
| A61B 5/0432 | (2006.01) | |
| A61B 5/091 | (2006.01) | |
| A61B 5/113 | (2006.01) | |

(52) U.S. Cl.
CPC .......... *A61B 5/6823* (2013.01); *A61B 5/7221* (2013.01); *A61B 5/7225* (2013.01); *A61B 5/7278* (2013.01); *A61B 5/0006* (2013.01); *A61B 5/0245* (2013.01); *A61B 5/0408* (2013.01); *A61B 5/0432* (2013.01); *A61B 5/0816* (2013.01); *A61B 5/0833* (2013.01); *A61B 5/0836* (2013.01); *A61B 5/091* (2013.01); *A61B 5/1135* (2013.01); *A61B 5/6831* (2013.01); *A61B 5/7203* (2013.01); *A61B 5/7246* (2013.01); *A61B 2503/10* (2013.01); *A61B 2560/0214* (2013.01)

(56) References Cited

OTHER PUBLICATIONS

Cottin, F., P-M. Leprêtre, and P. Lopes. "Assessment of Ventilatory Thresholds from Heart Rate Variability in Well-Trained Subjects during Cycling." Age (years) 20: 6-3 (Cottin).*

Nikooie, Roohollah, et al. "Noninvasive determination of anaerobic threshold by monitoring the% SpO2 changes and respiratory gas exchange." The Journal of Strength & Conditioning Research 23.7 (2009): 2107-2113 (Nikooie).*

Sullivan, Martin J., Michael B. Higginbotham, and Frederick R. Cobb. "Exercise training in patients with chronic heart failure delays ventilatory anaerobic threshold and improves submaximal exercise performance." Circulation 79.2 (1989): 324-329 (Sullivan).*

Gaskill, Steven E., et al. "Validity and reliability of combining three methods to determine ventilatory threshold." Medicine and science in sports and exercise 33.11 (2001): 1841-1848.*

F. Cottin et al. "Assessment of Ventilatory Thresholds from Heart Rate Variability in Well-Trained Subjects during Cycling", International Journal of Sports Medicine, Jan. 1, 2006, vol. 27, No. 12, pp. 959-967.

International Search Report dated Mar. 24, 2014 re: Application No. PCT/EP2013/074905.

J. Alberto Neder et al. "A Simplified Strategy for the Estimation of the Exercise Ventilatory Thresholds", Medicine and Science in Sports and Exercise, May 2006, vol. 38, No. 5, pp. 1007-1013.

Maria Christina Bisi et al. "Automatic detection of maximal oxygen update and ventilatory threshold", Computers in Biology and Medicine, www.elsevier.com, Jan. 1, 2011, vol. 41, No. 1, pp. 18-23.

Roohollah Nikooie et al. "Noninvasive Determination of Anaerobic Threshold by Monitoring the %SpO2 Changes and Respiratory Gas Exchange", Journal of Strength and Conditioning Research/National Strength & Conditioning Association, Oct. 2009, vol. 23, No. 7, pp. 2107-2113.

Written Opinion dated Mar. 24, 2014 re: Application No. PCT/EP2013/074905.

* cited by examiner

METHOD AND SYSTEM FOR DETERMINING A VENTILATORY THRESHOLD

FIELD OF THE INVENTION

The present invention generally relates to a method and system for determining the ventilatory threshold of a subject during fitness or athletic training.

BACKGROUND OF THE INVENTION

Monitoring of performance and physiological parameters is of importance for fitness and athletic training. The fitness industry has for long proposed devices for performance monitoring that are able to measure the distance, compute average/maximum speed.

Modern training computers (personal trainers) further determine the heart beat rate and incorporate training programs, and optionally integrate a GPS sensor for more precision in the performance monitoring. For example, the heart beat rate measurement is used in fitness and athletic training for determining working capacity or stress level.

Usual training protocols are based on zones related to percents of maximum heart rate (HRmax—the highest number of heart beats per minute an individual can reasonably achieve in a stress exercise). Training between 70% and 90% of HRmax is particularly important for improving the ability to sustain high exercise intensities. Such work rates tend to correspond to an important physiological change: the energy production pathway turns from an oxygen consumption (aerobic) mode to an anaerobic mode. That transition is called the anaerobic threshold (AT). Exercising at or above the transition is not possible for long since lactic acid accumulates in the tissues, leading to muscle pains and breath shortages. Equivalent terminology for the anaerobic threshold is either the lactate threshold or the ventilatory threshold, as a sudden rise of both lactic acid in blood and ventilation occurs at that point. Ventilation (or minute ventilation) is scientifically defined as the product of the breathing frequency and the volume of inhaled/expired air.

The anaerobic threshold is nowadays determined in special test laboratories by means of standardized protocols. The most classic way of assessing the AT is by assessing blood lactate continuously throughout the test and identifying the point where blood lactate begins to accumulate (also known as lactate threshold).

Another conventional method for determining the anaerobic threshold is the well known V-slope method developed by Karlman Wasserman, based on the evolution of the ratio of oxygen uptake ($V_{O2}$) to carbon dioxide output ($V_{CO2}$). Before the anaerobic threshold is reached, $V_{O2}$ and $V_{CO2}$ tend to rise at roughly the same rate, whereby a best-fit line through these points is close to 1. Once the AT is reached, $V_{CO2}$ will rise faster and the line fitting through the points corresponding to the anaerobic region will have a slope greater than 1. The intersection point between the two lines is thus the threshold between the aerobic and anaerobic regions. Since the threshold is determined from the ventilatory response, it is generally referred to as ventilatory threshold (VT).

Today, the VT or AT is a parameter that is primarily used in training endurance athletes to determine suitable training capacities, respectively monitor their training capacities.

When the heart beat rate value corresponding to the VT is known, a desired training capacity can be accurately maintained by means of continuous heart beat rate monitoring.

However, as explained above, the presently available methods for determining the AT or VT values are based on difficult lactic acid or breathing gas measurements, requiring taking of blood samples and expensive laboratory equipment and staff; in other words: using invasive and non-portable equipment.

It is thus desirable to have portable equipment that allows field measurement of the anaerobic threshold, so that athletes, sportsmen or fitness enthusiasts can monitor their VT during real-life and real-time exercise.

U.S. Pat. No. 5,810,722 assigned to the Polar Electro company describes a device for assessing a person's VT under a gradually increasing stress. The respiratory frequency and volume are calculated on the basis of the ECG signals to exploit a respiration frequency vs. heart rate graph, or a ventilation vs heart rate graph, where the VT appears as a break point. A difficulty related to this method is that it is entirely based on ECG signals. Indeed, determining the respiratory response from the ECG, although theoretically possible, requires a high quality signal, which may not always be compatible with field measurements.

DE 102 48 500 describes a method for determining the AT of a subject during exercise that can be implemented by a portable system. The breathing frequency is determined by means of an expandable belt encircling the sportsman's chest and including a strain gauge. The AT is detected as an increase in the breathing frequency, typically by comparing a current breathing frequency to a previously determined breathing frequency.

While the system described in DE 102 48 500 may be appealing in that it provides an in field VT sensor, which can be easily implemented, its scientific rationale has been criticized by some authors. For example, Cottin F. et al. in "*Ventilatory Thresholds Assessment from heart rate variability during an incremental exhaustive running test*", Int J Sports Med, 2006, ISSN 0172-4622, conclude that assessing the VT from the breathing frequency is not possible during a running test.

As a matter of fact, the determination of physiological parameters during the actual performance of physical activity in real-life is a challenge. A first difficulty is the reduced number of signals, since blood taking and classic laboratory equipment (spirometers etc.) cannot be used. A further difficulty is the quality of the signals measured with portable equipment. Obviously, this reduces the possible methods usable to determine the VT. Thirdly, it is desirable to be able to determine physiological parameter(s) such as VT during any kind of training or performance, and not only for pre-defined effort tests.

In this connection, it may be noticed that although a variety of papers discuss and compare methods for determining the VT, they typically rely on finished data sets obtained from a known population of athletes all performing the same pre-defined tests (see references 1-3). Hence, the classical approach followed in the literature consists in acquiring, during the performance of a standardized test, the experimental data for the test population, and then applying several methods to the experimental data, such as e.g.: respiratory exchange ratio, V-Slope, Ventilatory equivalent for $O_2$ . . . . Authors then have typically discussed the verifiability, repeatability and/or sensitivity of such methods, relying on statistics (e.g. mean and standard deviation).

BRIEF SUMMARY

The invention provides a reliable method and system for the in-field determination of the ventilatory threshold, in particular in real-time.

According to the present invention, a method of determining the ventilatory threshold of a subject (athlete, sportsman, fitness enthusiast, etc. . . . ) is proposed, wherein data relating to physiological parameters of a subject are acquired during an exercise session, including at least data reflecting the subject's respiration and heart beat pulses, and storing said data in function of time. The acquisition of these data can be done by direct or indirect measurements, and/or possibly involve estimations.

A ventilatory threshold value is determined for the given exercise session according to two different approaches, i.e. using two different principles to determine the ventilatory threshold (VT). As it will be explained below, the method is particularly adapted for determining the ventilatory threshold in real-time during the course of an exercise session.

It shall further be appreciated that a confidence index is determined for each of the first and second values of ventilatory threshold. This confidence index is advantageously based on one or both of the following criteria:

1. the detectability of the ventilatory threshold: the idea is to characterize the ease of identification of the VT from the data set. The more manifest the VT, the better the confidence index.

2. the matching between the value of ventilatory threshold according to one approach and that according to the other approach. This criteria thus evaluates the similarity or proximity between the current VT and that computed according to another approach.

An interesting aspect of the present invention is hence the determination, together with a VT value, of a confidence index that gives an indication of the accuracy or reliability of the determined VT value. Indeed, it appears from the prior art that a variety of methods exist to determine the VT or AT. In the laboratory environment, the physiological data recorded during effort are analyzed by MDs who determine the AT and VT "visually". Besides, programs have been developed to assist MDs in the analysis of effort data, namely by fitting the test data through linear regression analysis. However, despite such programs, as of today the final decision is still made by an MD.

Another interesting aspect of the invention is the systematic and automatic (i.e. computer-assisted) evaluation of the VT by at least two approaches. Indeed, one or more additional VT values may be determined on the basis of measured, statistical or historical data. The most reliable VT may then be selected on the basis of its respective confidence index. It shall thus be appreciated that the determination of the confidence index is here carried out in a systematic manner by the control unit, as an inherent feature of the method, for the purpose of self-assessing the reliability/ accuracy of the VT determination during a same exercise session.

As a matter of fact, the steps of determining the VT values according to the two approaches together with the respective confidence indexes is part of a VT Determination Routine that may be implemented periodically during an exercise session, e.g. at intervals between 1 and 10 seconds.

In practice, the finally selected VT is preferably outputted (typically displayed) to the user together with the respective confidence index. The VT is typically expressed as a time value and/or a HR value corresponding to the moment when the VT occurred. A sound may also be emitted when the VT is reached, so that the sportsman knows that he has crossed the VT.

The determination of the confidence index, in accordance with the present invention, is very convenient in the case of in-field monitoring devices. It allows a periodic determination of the VT in real sports conditions and throughout the whole exercise duration. Since the confidence index is displayed periodically to the user, he will know when a VT value should be really accurate or when it has a low confidence index, and he should thus await a further determination.

It should be understood here that when the present method is implemented in the field, the VT Determination Routine is carried out periodically, at pre-set intervals, on measured data at any time of the exercise session, where the actual effort is unknown (i.e. the VT determination may be performed at a time where the sportsman has not yet reached the VT). This is very different from prior art situations where the VT is determined from a finished data set, at the end of progressive or other standard test, and were it is known that the VT has occurred. Hence, as mentioned above, the periodic and automatic calculation of the confidence index each time the VT value is computed during a same and given exercise session, permits an assessment of the calculated VT value, thereby indicating its level of reliability.

The present invention has important practical benefits:

Athletes and sportsman can monitor their VT on a daily basis, without any lab effort. This is of great interest for elaborating their training programs. Indeed, the determination of AT/VT during and/or directly after physical effort enables better improvement of the endurance. The direct feedback on the ventilation and heart rate can be used to immediately adapt the activity towards better performance.

For example, the direct knowledge of the AT/VT is a great asset to adapt the activity to the "of-the-day" fitness level of the athlete, thus to overcome the risk of overtraining and recurrent fatigue if the athlete is not at his usual physical level (disease, dehydration, stress . . . ).

The present method only requires a respiration sensor and a heart rate monitor, so that it can be easily implemented in a portable device allowing monitoring the athlete in real conditions and throughout an unlimited period of time.

The present method also permits near instantaneous detection of the ventilatory threshold once it is reached, and therefore allows the direct modification of the effort for better training and better performances during a competition event.

As it will be understood by those skilled in the art, the VT can be determined from various data representative of physiological parameters linked to respiration and/or heart beat rate. Due to the physiological phenomenon occurring at the VT, in many instances the threshold corresponds to the intersection point between the pre and post-VT tendencies. Typically one may run a double or multi-linear regression on the data set and thus identify the intersection point (break point or deflection point). In the context of the present invention, the detectability of the VT may thus be characterized by the ratio of the slope of the post-VT line (anaerobic) over the slope of the pre-VT line (aerobic). The greater this slope ratio, the more manifest the threshold, and hence the better the detectability.

A grade may thus be attributed to a calculated VT that reflects this detectability, the greater the slope ratio, the better the grade.

Another grade may thus be attributed to reflect the matching between VT values obtained by different approaches. Preferably, this matching grade can be determined on the basis of the following relationship:

$$\frac{VTi - VTo}{VTi}$$

where $VT_i$ is the ventilatory threshold according to the current approach, and $VT_o$ is the ventilatory threshold according to the other approach.

The confidence index may thus be calculated from at least one of the detectability grade and matching grade, and may further take into account other grades, such as e.g. one or more grades reflecting:
- the number of available data for calculation in each approach;
- the sum of residuals and the dispersion of the data after filtering;
- the probability of perturbation due to a warm-up threshold (initial deflection of the data);
- the matching with earlier calculated values of ventilatory threshold according to the same approach for the same exercise session
- the matching with statistical data of ventilatory threshold.

Preferably, the first ventilatory threshold ($VT_1$) is determined, according to the first approach, from data representative of ventilation vs. heart beat rate, as the breakpoint at which ventilation starts increasing more rapidly than the heart beat rate. The ventilation vs. HR analysis has proved to be reliable and happens to be a convenient referential for in-field VT determination.

In one embodiment, the second ventilatory threshold ($VT_2$) is determined, according to the second approach, from data representative of ventilation vs. time, as the breakpoint at which the ventilation starts increasing more rapidly.

It may be noted that in these approaches the term ventilation is meant to reflect a ventilation rate depending on a breathing frequency and volume, as is conventionally understood in the art.

Preferably, data indicative of breathing frequency and of breathing volume, and hence of ventilation, are determined by a respiration sensor worn by the subject, the respiration sensor comprising preferably at least one elongation sensor.

In particular, the respiration sensor may comprise a chest sensor, preferably an expandable belt encircling the subject's chest with an elongation sensor integrated therein. An additional abdominal sensor may be used, also preferably comprising an expandable belt encircling the upper abdominal region of the subject with an elongation sensor.

According to another aspect of the invention, there is proposed a system for determining the ventilatory threshold of a subject.

The invention is preferably implemented to be portable. In such case, the method can be implemented by a processing unit, which can be integrated in a wristwatch or in a portable device, e.g. a mobile telephone, tablet or dedicated device. In such case the transmission between the sensors and the processing unit is preferably wireless, although a wired connection is possible. Any appropriate wireless connection may be employed, preferably Bluetooth. Alternatively, the ventilation and heart rate data could be stored during exercise for later processing, in accordance with the method of the present invention.

Also, it may be noted that while the heart rate and respiration sensor have been described as incorporated in a belt, they could be integrated in sports clothes and/or underwear.

According to a further aspect the present invention proposes a method for determining a breakpoint in a physiological data set acquired during exercise, said method comprising a fitting step comprising identifying two lines with a different slope that fit selected data from the physiological data set, wherein said breakpoint corresponds to the intersection of said lines. The method comprises a preliminary filtering step, wherein the physiological data set is processed in order to eliminate data corresponding to recovery or stable periods during the exercise session and keep only growing trends as the selected data. The resulting data thus represent an incremental effort, which is preferably processed with a best-fit algorithm, and the second ventilatory threshold ($VT_2$) is determined from these data as the breakpoint at which the ventilation starts increasing more rapidly.

An aspect of the present invention concerns a computer program comprising instructions that cause a processor to carry out the method as described hereinabove, when the program is executed on a processor. Such computer program may be provided as part of a computer program product, including a carrier, e.g. a data storage device (such as a hard disk, an optical storage disk, a memory stick or card, embedded in a memory or the like) or of a carrier signal (e.g. a digital or analog communication signal), carrying the computer program.

BRIEF DESCRIPTION OF THE DRAWINGS

The present invention will now be described, by way of example, with reference to the accompanying drawings, in which.

DETAILED DESCRIPTION OF A PREFERRED EMBODIMENT

The present method and apparatus provide a convenient way of determining the ventilatory threshold (VT) of a person (athlete, sportsman, enthusiast . . . ) in the field, i.e. during exercise. More particularly, the present method and system are designed so as to determine the VT according to at least two approaches based on measured data relating to at least one physiological parameter, preferably reflected from data indicative of the respiration and/or of the heart beat rate. Then a confidence index is calculated for each VT, which reflects the estimated reliability of the determined value. The final value of the ventilatory threshold may then be based on the confidence index.

In the following, a preferred embodiment of the present system and method will be described, wherein the system is conveniently designed to be portable and is configured to combine three approaches for determining the VT.

Figure 1:
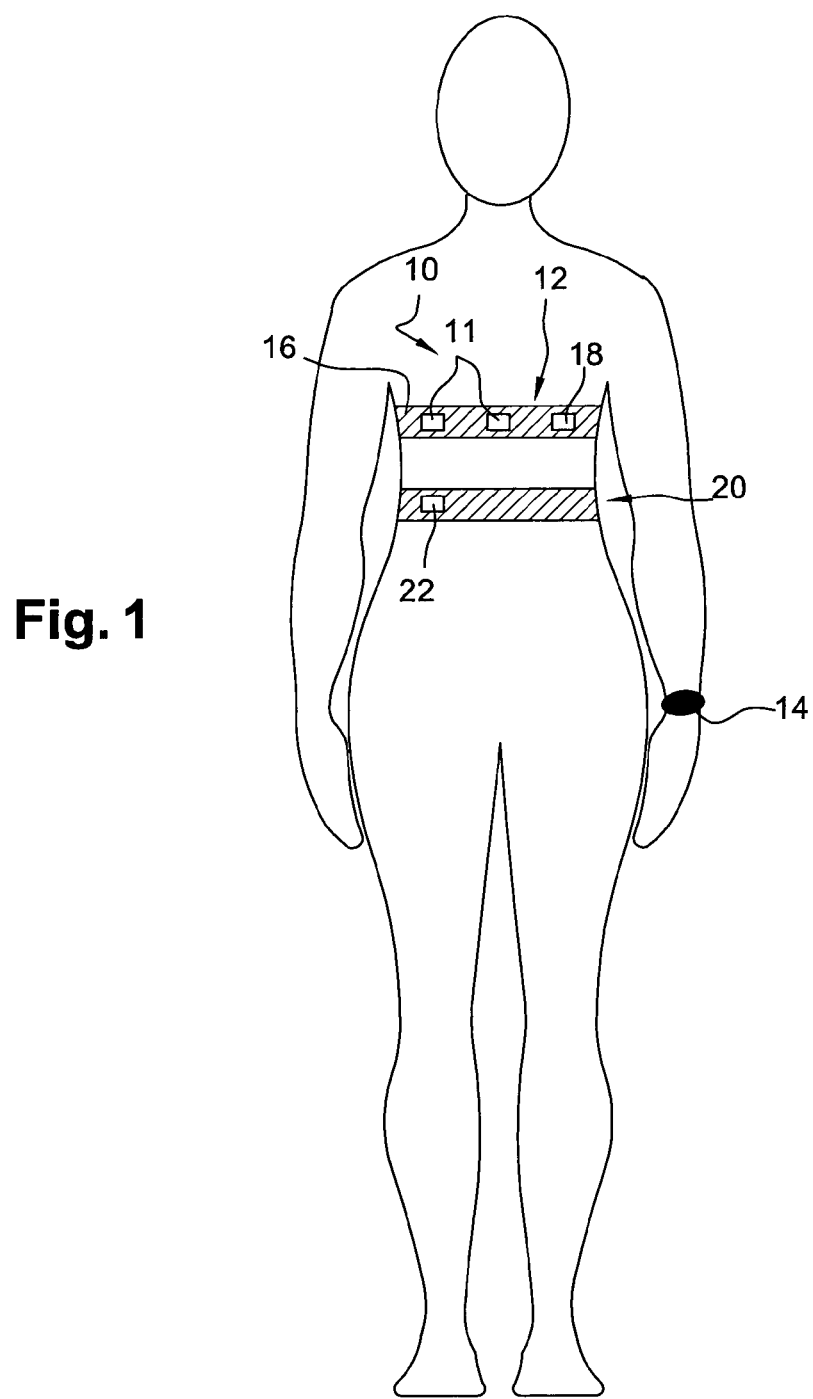
FIG. 1: is a schematic diagram of the components of one embodiment of the present system.

FIG. 1 illustrates a possible set-up of the present monitoring system for determining the VT. In the present embodiment, the system comprises three main components: a heart rate sensor 10, a ventilation sensor 12 and a control unit 14. The heart rate sensor 10 comprises at least a pair of ECG electrodes 11 that are, in use, to be appropriately located on the subject's chest. These electrodes can be based on any appropriate technology, as e.g. used in conventional heart rate monitors. The measured ECG signals can be processed in the control unit 14, or in a dedicated processor integrated within the sensors, in order to extract the heart beat pulses and/or rate. The hardware and signal analysis of ECG monitors is widely known in the art and this will therefore not be further detailed herein.

The ventilation sensor 12 preferably comprises an expandable belt 16 encircling the subject's chest in order to follow the chest deflection, hence forming the chest sensor. The belt 16 includes an elongation sensor 18 in order to follow the extension and contraction of the belt, for which any appropriate sensor technology may be used. The elongation sensor 18 may e.g. be based on resistive, inductive or capacitive technology, so that chest deflection/expansion during breathing changes the belt's length and hence causes a modification the sensor's impedance, which may be observed from the delivered sensor signal. Preferably, the elongation sensor is of the inductive type and includes a sensor wire, whereby chest deflection causes a modification in the sensor's inductance.

The electrodes 11 of the heart beat sensor 10 may be conveniently integrated in the expandable belt 16, as shown in FIG. 1.

The system may include another belt sensor 20, referred to as abdominal sensor, preferably with same or similar elongation sensor 22, e.g. here with an inductive wire sensor.

It is thus possible to monitor two respiratory responses during exercise: from the chest sensor 18 and optionally from the abdominal sensor 22.

The heart beat data and respiration data sensed by the various sensors are transmitted to the control unit 14, here embodied as a wristwatch. The form of the control unit is not critical, but is preferably designed as a self-contained portable device, with a battery, a display, a command interface and a sensor interface for a wired or wireless connection. For convenience, wireless communication between the various sensors and the control unit is preferred, e.g. using the Bluetooth protocol.

The control unit 14 is configured to receive the input data coming from the heart rate sensor 10 and respiration sensors 18, 22. The heart beat rate (HR) is stored vs. time in a memory in the control unit.

Figure 6:
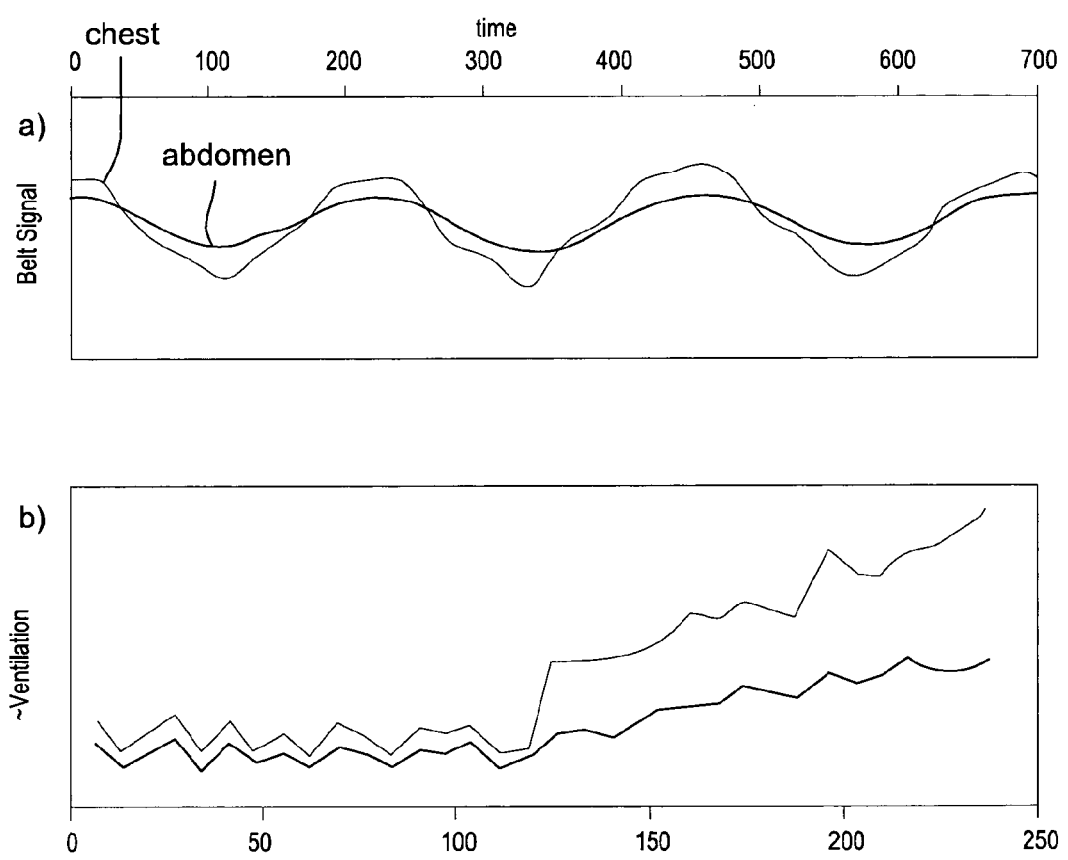
FIG. 6: shows: a) graph of the chest and abdominal sensor signal vs time, and b) of the corresponding ventilation vs time.

As regards the respiration sensors 18, 22, they typically deliver an alternating signal, as e.g. illustrated in FIG. 6 *a*), which varies with the chest deflections. The breathing frequency can be easily determined from the wave period. The signal's amplitude is related to the inspired and exhausted amount of air. Hence, the signal delivered by the respiration sensor allows determining the breathing frequency and a value indicative of the current breathing volume. Multiplying these latter values gives an indication of the ventilation, which is in accordance with the dimension of the classical definition of ventilation (i.e. breathing frequency×tidal volume—also referred to as minute volume). This ventilation calculation can be perfected by taking into account the height and/or circumference of the user's chest, which can be directly inputted by the user or deduced based on the user's weight or height or from the size or type of clothes/gear of the user.

In a preferred embodiment, the control unit 14 is configured to periodically process the input data in order to calculate the ventilatory threshold. This determination is carried out in the present embodiment using a VT Determination Routine with three different VT determining approaches, with respective confidence indexes, as will now be explained in detail with reference to FIG. 2.

Figure 2:
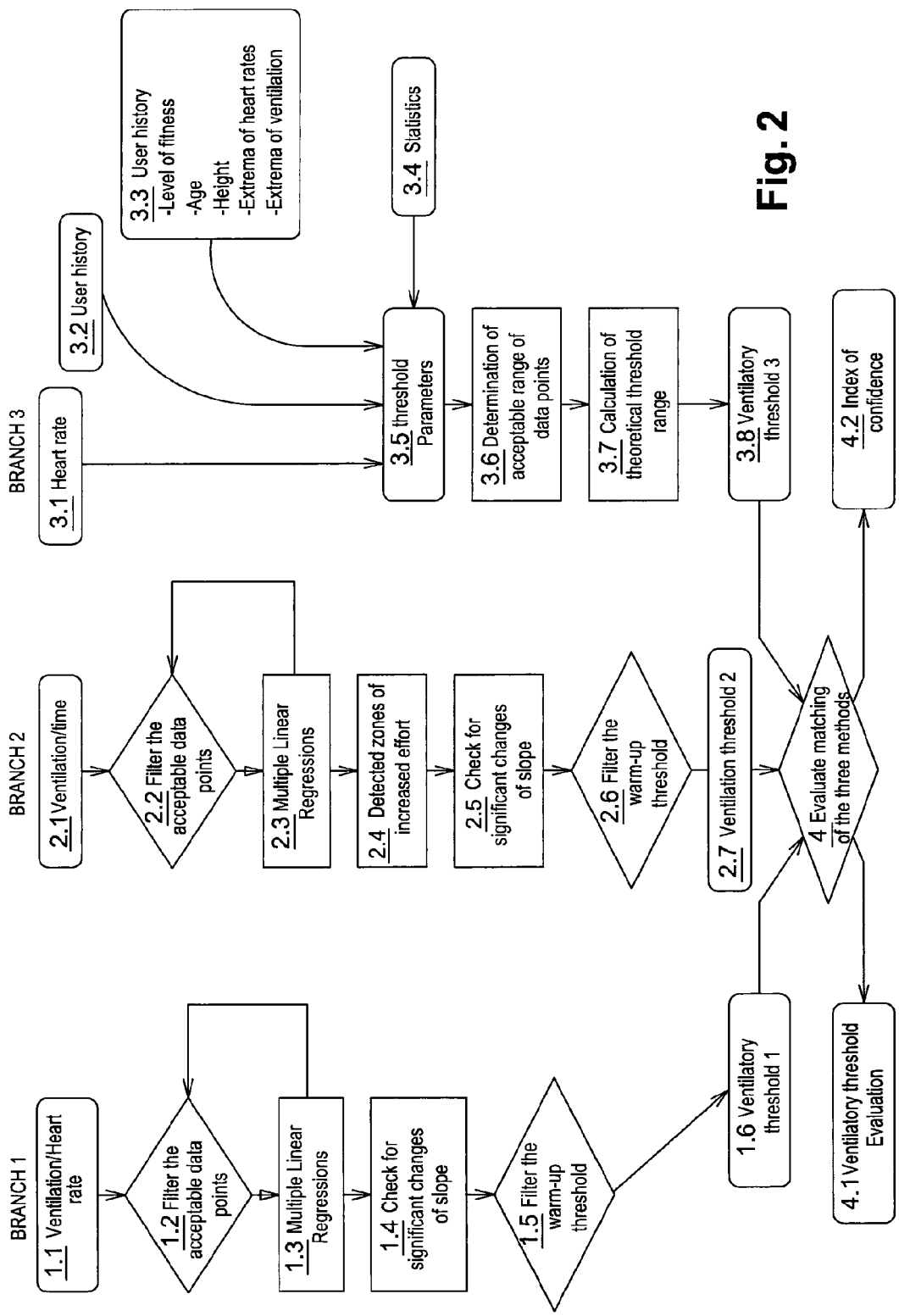
FIG. 2: is a flowchart of one embodiment of the present method.

The flow chart of FIG. 2 clearly shows the processing along three branches:
- branch 1 implements the $1^{st}$ approach and relies on a ventilation vs. HR analysis;
- branch 2 implements the $2^{nd}$ approach and relies on a ventilation vs. time analysis;
- branch 3 implements the $3^{rd}$ approach and is based on a statistical analysis, preferably taking into account user history.

Each branch provides a respective VTi value with an associated confidence index IDXi. The values $VT_1$, $IDX_1$ and $VT_2$, $IDX_2$ corresponding to branches 1 and 2 are recalculated periodically, as new data are acquired/measured during exercise. As regards branch 3 however, since this approach is statistical and possibly based on user history, the values will normally not change for the current exercise period.

A prerequisite for running approaches 1 and 2 is of course the acquisition of a data set. As explained above, the signals delivered by the heart rate electrodes are processed in the control unit 14 to extract the heart beat pulses and then rate, which are stored in function of time. The signals delivered by the ventilation sensor(s) are processed to produce data corresponding to the subject's ventilation in function of time. It may be noted here that while in the present embodiment the sensor signals are transferred as raw data, where the desired heart beat rate, breathing frequency and volume are determined in the processor unit, the relevant physiological parameters can alternatively be directly calculated in processors associated with the sensors, so that a heart rate value and ventilation value can be directly transmitted, periodically, to the control unit. This would reduce the amount of data to be transferred to the control unit.

Conveniently, the control unit 14 may thus comprise a table storing data representing measured values of: heart rate and respiration, preferably ventilation, in function of time.

1. BRANCH 1—VENTILATION VS. HR APPROACH

1a. Calculating the VT

Branch 1 implements a ventilation vs. heart beat rate (HR) approach. The acquired data series of ventilation and heart beat rate are processed to extract a VT value, noted $VT_1$. As it will be understood by those skilled in the art, the data represent a cloud of points (see FIG. 3), since several ventilation values may correspond to a given HR value.

Although being not usual in the art, this approach is considered to have some merits since the pulse rate and the work rate are mostly linearly dependent on each other. Also, the ventilatory response depends on the work rate. Hence, one may relate the VT to the HR.

To be more precise, during exercise in aerobic state (after a so-called warm-up threshold appearing at the beginning of exercise), ventilation (VE) and heart rate (HR) are closely correlated: they increase in response to an increase of physical activity. However, it can be observed that when the effort increases above the ventilatory threshold, the response of the heart and the respiratory system start to be different. In most cases, the ventilation system will have more margin to increase than the heart: both the breathing frequency and the instant volume will likely increase dramatically. Consequently, at the ventilatoty threshold, VE will grow faster than HR. In graphical terms, this means that the curve VE/HR will have a slope change at the ventilatory threshold.

In this first approach, the VT is thus determined as the heart rate at which ventilation starts increasing more rapidly than heart rate. The VT corresponds to a breakpoint or deflection point. The computer-assisted determination of such breakpoint is classical in the art, and can be performed by mathematical analysis, generally through linear regression analysis. This step is indicated 1.3 in branch 1. Accordingly, the data set (VE; HR) is processed to identify two straight lines fitting the points over respective heart rate ranges, each with a good correlation coefficient. The point where these lines intersect is the VT. From lower HR to the VT, the organism operates in the aerobic region, and the line leading to the VT is herein referred to as the aerobic line. For ease of expression, the line after the VT is referred to as anaerobic line, although it may not be scientifically rigorous.

Figure 3:
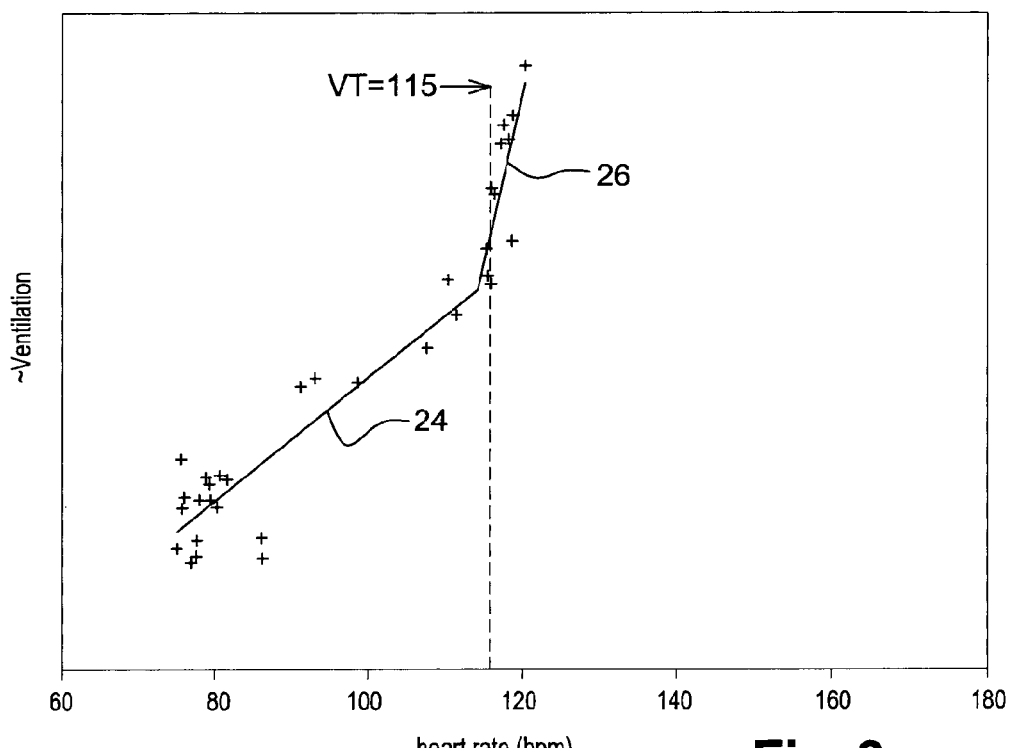
FIG. 3: is a ventilation vs. heart rate plot used in the first approach.

In the exemplary plot of FIG. 3, the multiple regression analysis has resulted into aerobic line 24 and anaerobic line 26 that intersect at HR=115, which is thus considered to be the VT.

As can be seen in FIG. 2, branch 1 includes a preliminary filtering step 1.2, where the data set are analyzed and suspicious data are discarded. For example, the filtering step may retain data that fall within a prescribed range of heart rate, say e.g. between 35 and 250 beats per minutes. Preferably, this range is refined from the input of branch 3, in particular from step 3.6. The data points which are too far away from the trend may thus be discarded. The quality of the data will also be assessed at this step (see below).

The next step is the linear regression step 1.3, followed by the slope-checking step 1.4, where changes of slopes between the best fitting straight lines are detected. In practice, the treatment algorithm may be designed to search for two lines, where both lines have a positive slope and the second, anaerobic line has a greater slope than the first, aerobic line. A ventilatory threshold may be suspected when there is a significant increase in the slope. For this purpose, the algorithm may be designed to conclude to a VT only if the ratio of the second slope over the first slope exceeds a predefined slope threshold, or falls within a predetermined slope range. The characteristic of this change of slope illustrates the detectability of the VT and is advantageously used to compute the index of confidence.

The filtering step 1.2 may be repeated if desired.

It may be noted that at the beginning of the effort, a change of trend is likely to be seen, which could look like the ventilatory threshold, but this is only a minor threshold corresponding to the warm-up phase of the athlete. Step 1.5 is provided to filter out this warm-up threshold. Hints that a warm up threshold is observed are that the considered VT value occurs:
  early in the exercise;
  at a low heart rate;
  with relatively low ventilation amplitude.

The probability to be at the warm-up will be taken into account in the confidence index.

The value of step 1.6 is thus a VT value, expressed in heart beat rate, that has passed the warm-up filtering step 1.5. It is noted $VT_1$.

1b. Calculating the Grades

The confidence index associated with the above determination of VT is preferably based on a set of grades, that can all be summed up, optionally with a respective coefficient, to determine the final index value $IDX_1$ for branch 1 for each iteration of the VT Determination Routine during the exercise session.

In the present method, the following grades are advantageously taken into account for calculating the first confidence index $IDX_1$.

Grade N_1:
The grade is based on the number of data points available for branch 1 during the current exercise session, typically after filtering step 1.2. The greater the number of data points, the higher the grade.

Grade Q_1:
Grade Q_1 reflects the quality of the data in branch 1 and is obtained by assessing the dispersion of the data. For example, the grade may depend on the total sum of residuals and on the quality of the sampling after the outliers have been filtered. The lesser the sum of residuals, the better the grade.

Grade S_1:
This grade is attributed to illustrate the detectability of the VT, which is preferably achieved by characterizing the importance of the slope increase at the ventilatory threshold. A ratio between the slope of the aerobic slope and post-VT slope is calculated, and compared to predefined threshold(s) or ranges, and a corresponding grade attributed. The greater the slope ratio, the higher the grade.

Grade W_1:
Grade W_1 reflects the likelihood that the VT calculated in branch 1 may be disturbed by the presence of the warm-up threshold. It determined on the basis of the distance between the calculated VT and the estimated position of the warm-up threshold (WT) both in units of time and heart rate. The higher the grade, the lower the WT induced perturbation.

Grade R_1:
This grade reflects the robustness of the algorithm over time. It is calculated on the basis of the average of the difference between the current value of the ventilation threshold ($VT_n$) and values that were calculated earlier within the same branch:

$$\frac{1}{n-1}\sum_{i=1}^{n-1} \alpha_i |VT_n - VT_i|$$

$VT_i$ represents the (n−1) VT values determined earlier during the exercise session and $\alpha_i$ is a coefficient related to the corresponding confidence index retained at the end of iteration i of the VT determination routine. The greater the confidence index, the greater alpha $\alpha_i$. For example, $\alpha_i$ may be computed as [confidence index (i)/100]$^3$.

By way of this formula, the results of the preceding VT determinations made during the course of the exercise session are taken into account to improve the VT determination corresponding to the current iteration of the VT Determination Routine.

The smaller this average value, the higher the grade.

2. BRANCH 2—VENTILATION VS. TIME APPROACH a) Calculating the VT

The ventilation vs. time is a conventional plot to determine the VT. Here again we have a set of data points (VE; time), and the point of interest is the breakpoint where the ventilatory slope starts increasing more rapidly than time. Conventionally, this can be easily determined by double linear regression, the VT corresponding to the intersecting point between the two lines.

Figure 4:
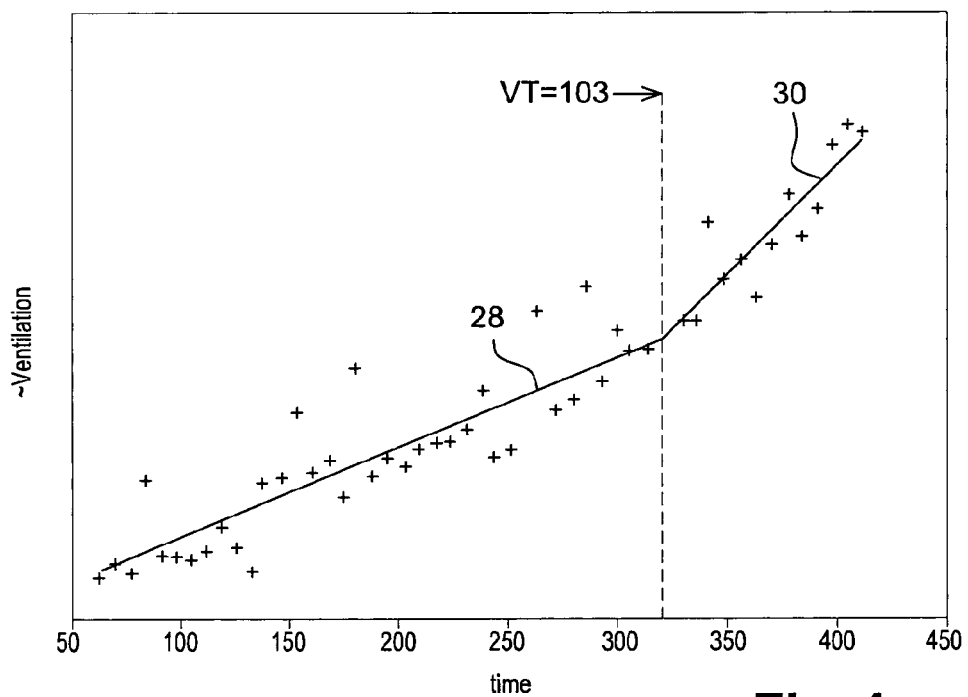
FIG. 4: is a ventilation vs. time rate plot used in the second approach.

An exemplary ventilation—time plot is illustrated in FIG. 4. The VT is the point—brake point or deflection point—at the intersection between the aerobic line 28 and the anaerobic line 30. It may be noticed that while the abscissa in FIG. 4 is the time, the VT is preferably expressed in terms of heart beat rate. Once the time of the breakpoint has been found, the corresponding HR can indeed be read from the memory since for every time stamp ventilation data and HR data are recorded.

Branch 2 may thus be implemented in a manner similar to Branch 1, to include the following functions:
a filtering step 2.2 similar to step 1.2 in FIG. 2 to filter out suspicious data; a multiple linear regression analysis 2.3 step to identify the aerobic and anaerobic trends;
a slope checking step 2.5 to assess the slope increase and validate the VT upon identification of a significant slope increase for the anaerobic trend (relative to the aerobic trend), similar to step 1.4;
a warm up threshold filtering step 2.6 similar to step 1.5.

A peculiarity here, however, is that when the monitoring is done during a nonstandardized test with increasing efforts, the subject may e.g. reduce his pace or performance to recover from the effort, or run along a downward track. Accordingly, the ventilation vs. time plot may comprises a plurality of peaks of various heights, which makes it difficult to identify the aerobic and anaerobic trends in the ventilation vs. time plot.

Figure 5:
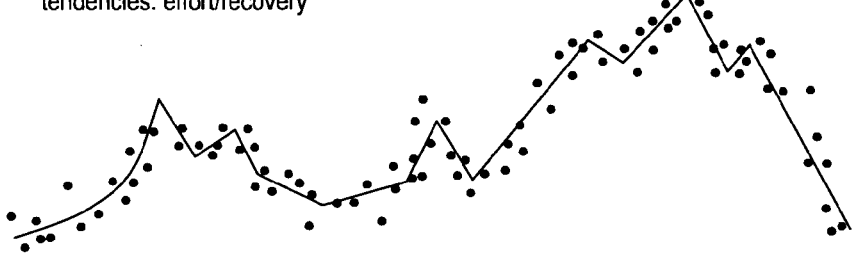
FIG. 5: are ventilation vs. time plots illustrating the data reconstruction principle.
Figure 5:
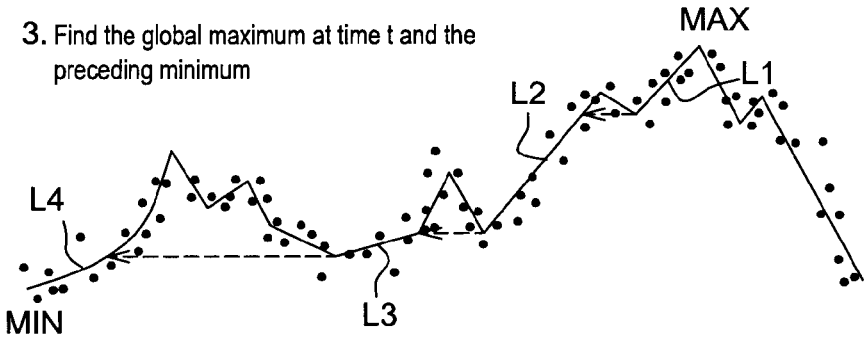
Figure 5:
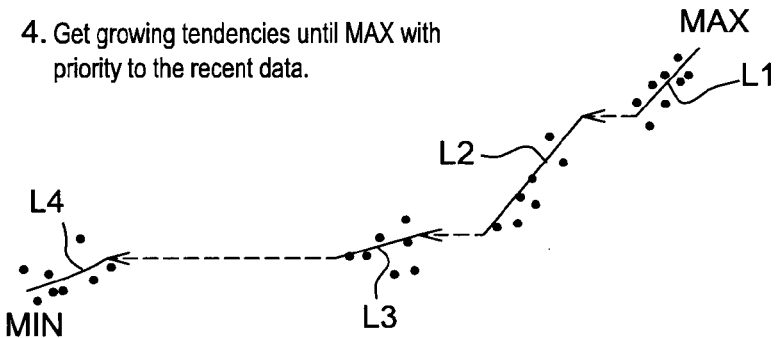
Figure 5:
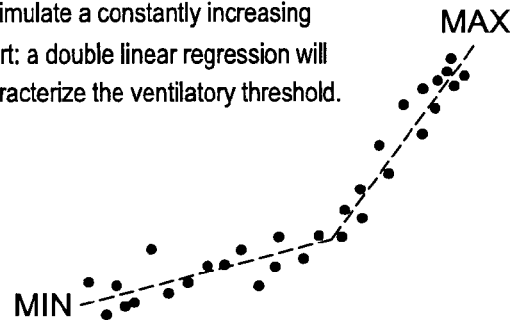

To attend this matter, branch 2 advantageously includes step 2.4, which aims at detecting zones of increased effort in the ventilation vs. time approach. FIG. 5 a) illustrates such a ventilation vs. time plot that correspond to an effort with increasing efforts and recovery periods. The data points have been processed with a multi linear regression algorithm to detect a line for each trend. Again, such multiple linear regressions are conventional and need no further explanations.

Then the reconstruction algorithm identifies the Maximum peak (MAX in FIG. 5b), identifies the growing line (noted L1) leading to the MAX, and proceeds backwise in searching the previous growing line (L2) containing an ordinate equal to the minimum ordinate of the current line (L1) reaching the MAX. Next, starting from growing line (L2), the algorithm searches for a previous growing line (L3) containing an ordinate equal to the minimum of the current growing line (L2). This procedure is repeated up to the earlier growing line (L4). In doing so, peaks corresponding to local efforts with corresponding recovery periods can be eliminated.

After the desired growing tendencies are identified, the corresponding data points are used to simulate a constant increasing effort, which can be simply characterized by a double linear regression, where the aerobic and anaerobic lines intersect at the VT, as shown in FIG. 5 d). In doing so, priority may be given to more recent data.

The obtained ventilatory threshold, expressed in HR, is noted $VT_2$.

2b. Calculating the Grades

In this approach, five grades N_2, Q_, S_2 W_2 and R_2 are preferably attributed on similar principles as for grades N_1, Q_1, S_1, W_1 and R_1. Again, these grades are calculated for each iteration of the VT Determination Routine.

3. BRANCH 3—STATISTICAL APPROACH a) Calculating the VT

This third branch exploits statistics and preferably user history (if available) to provide at least one reference VT value, noted $VT_3$. In FIG. 2, 4 possible data sources are indicated:

3.1. Heart beat rate: the current heart rate of the user is traditionally used as the basis to judge on the level of the activity of the athlete depending on its fitness level. If the fitness level is unknown, the heart rate at rest and during the activity can be used to assess the fitness level of the athlete. In case of good ECG signal, the micro changes of heart rate can also be used to assess the heart rate variability and determine therefrom the subject's fitness level, as is known in the art.

3.2. User history: the range of heart rate, ventilation and ventilatory threshold, which have already been measured during previous exercise sessions and stored is taken into account for determining $VT_3$.

3.3. User characteristics: the user characteristics can be entered by the user and some of them are estimated by the algorithm.

For example, the level of fitness can be either manually entered, estimated from the user history or taken from a default value which depends on the product used (ex: size of the belt/tshirt, typical market etc.). The gender, birthdate height and weight can also be asked to the user as input.

3.4. Statistics:

Different studies exist on the physiological parameters: the heart rates and fitness level can be estimated from the age of the person and his level of fitness using existing formulae.

For example, HRmax may be estimated as: HRmax=220−age (male) and HRmax=226−age (female).

Another know HRmax estimation, by Inbar, corresponds to: HRmax=205.8−0.685*age.

Step 3.5 then estimates the threshold parameters. The analysis of the data coming from 3.1-3.4 allows giving a rough characterization of the threshold by e.g. estimating the warm-up threshold and possibly other extreme values of VT by varying HRmax.

Step 3.6 relates to the determination of the acceptable range of points. The threshold parameters assessed in 3.5 are used to qualify acceptable data from the respiration sensors. For example, data outside of the acceptable range will be considered as noise and discarded: it is a supplementary way of removing outliers.

Finally, conventional formulae considered to be statistically relevant are used to estimate the VT in step 3.7. Depending on the number of statistical methods, one, two or more VT values are obtained.

For example, Polar Electro and David Swain have studied the predictability of the VT depending on HRmax and on the subject's fitness/training level. Table 1 summarizes these results. It can be seen that according to Polar, VT3 can be estimated as 80.5 of HRmax for a trained person. According to Swain, $VT_3$ for the same person would be 85% of HRmax.

TABLE 1

| | VT as a percentage of HRmax | |
| --- | --- | --- |
| Level | Polar VT as % of HRmax | Swain VT as % of HRmax |
| Untrained | 65 | 72.2 |
| Trained | 80.5 | 85 |
| Highly-trained | 94.6 | 94.6 |

The $VT_3$ value corresponding to branch 3 may then be calculated based on these one or more VT values, preferably as an average value.

Its confidence index may depend on the availability and coherence of the user info and history.

b. Calculating the Grades

The confidence index of the third approach may be calculated based on the two following grades.

Grade NP_3:

This grade increases with the number of parameters available to estimate the level of fitness: self judgment of the user (age, height, weight . . . ), gender, previous VT with good confidence index, and heart rate at rest . . . .

Grade M_3:

This grade reflects the matching between the user indicated fitness level and the fitness level that can be deduced from statistics e.g. based on the resting heart rate. The greater the discrepancy, the lower the grade.

4. MATCHING EVALUATION AND CONFIDENCE INDEX

In addition to the above grades, a further grade is advantageously attributed to characterize the matching of one approach with respect to another.

Grade MX__12 characterizes the matching between the VT calculated in branch 1 and 2. It is represented by the relative difference between both values and may thus be computed as: $(VT_2-VT_1)/VT_1$.

Grade MX_13 then similarly represents the matching between $VT_1$ and $VT_3$; and MX_23 between $VT_2$ and $VT_3$.

Confidence Index

The confidence index of each branch may thus be calculated based on the following relationships:

Confidence Index for the First Branch/Approach:

$$IDX1=c11*N\_1*Q\_1+c21*S\_1+c31*W\_1+c41*R\_1+c51*MX\_12+c6\_1*MX\_13$$

Confidence Index for the Second Branch/Approach:

$$IDX2=c12*N\_2*Q\_2+c22*S\_2+c32*W\_2+c42*R\_2+c52*MX\_12+c6\_2*MX\_23$$

Confidence Index for the Third Branch/Approach:

$$IDX3=c13*NP\_3*M\_3+c23*MX\_13+c33*MX\_23$$

where cXX are calibratable coefficients that are preferably chosen such that the final index can vary between 0 and 100 for each branch.

It will be understood that one could alternately compute confidence indexes with only part of the above grades, however preferably keeping the grades relating to the threshold detectability (Grade S_1) and the inter-approach matching (MX_ii).

Final Values

The ventilatory threshold selected/retained by the algorithm will be the one with the highest index of confidence.

In case of a draw (equal values), the number of the branch will give the priority.

The VT is calculated in units of heart rate and of time: at each time step, if the algorithm finds a VT, it will find the corresponding heart rate and time, and can therefore give an idea on the zone in which the athlete is currently in.

The heart beat rate corresponding to the selected VT can thus be given to the athlete/subject, with the respective confidence index.

By way of the present method, where the VT Determination Routine is performed at periodic (pre-set) intervals, the sportsman can thus have a periodic indication of his physical condition, and especially of his VT during the exercise session. As explained above, the VT value is periodically re-assessed during the exercise session, and the VT value is displayed (expressed as a time or heart beat rate) together with a confidence index, which additionally gives to the sportsman an information of the reality/accuracy of the displayed value.

5. EXAMPLES

FIGS. 7 to 10 relate to 4 exemplary tests corresponding to different situations, and illustrate the functioning the present method. For each case, in the corresponding Figure, the following graphs are shown:

a) HR and ventilation vs time (raw data);
b) Ventilation vs HR;
c) Ventilation vs. time (after processing branch 2—with elimination of recovery periods).

These graphs are shown here for the purpose of explanation but would normally not be shown to the user. The $VT_3$ values of branch 3 are not detailed with respect to these figures, but are taken into account in the confidence index calculations as explained above.

The finally selected value of VT is displayed in the top box, together with the confidence index.

Figure 7:
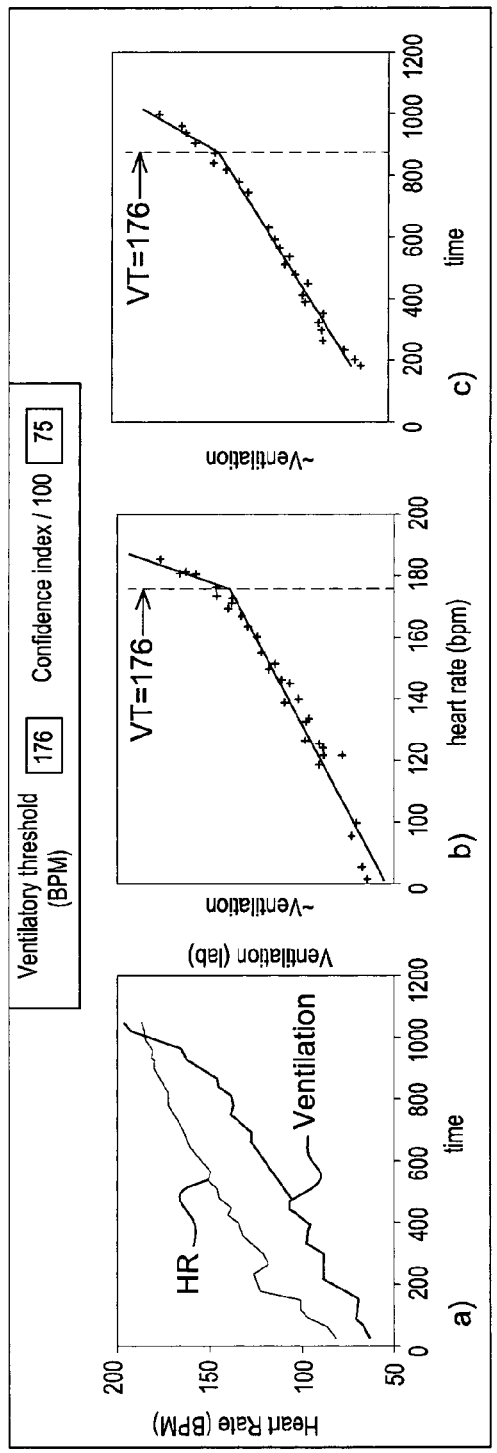
FIGS. 7 to 10: are graphs sets corresponding to specific examples, and showing a) HR and VE vs. time; b) VE vs. HR according to branch 1; c) VE vs. time according to branch 2.

Example 1—FIG. 7

The data have been obtained with a highly trained cross country skier. A VT of 176 bpm is found very soon after the ventilatory threshold it has been reached, with a good confidence index of 75%. This is the VT originating from branch 1.

Figure 8:
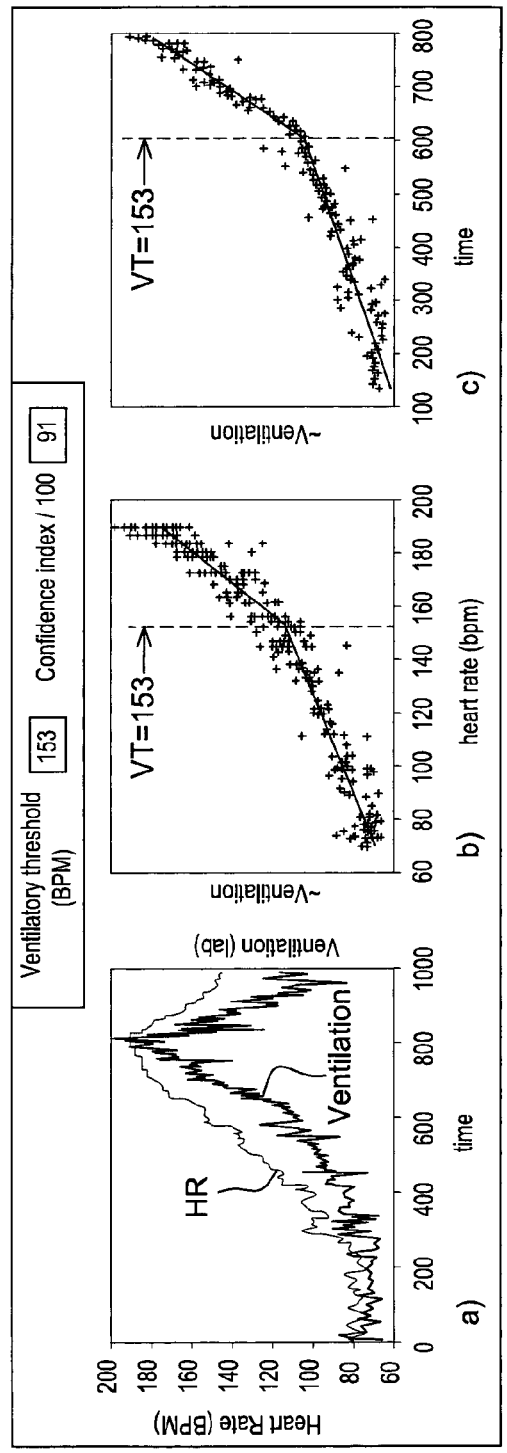

Example 2—FIG. 8

FIG. 8 show data obtained with a trained fitness enthusiast. In this case, the VTs of all three methods converged. A VT of 153 with good confidence index of 91 was displayed (originating from branch 1).

Figure 9:
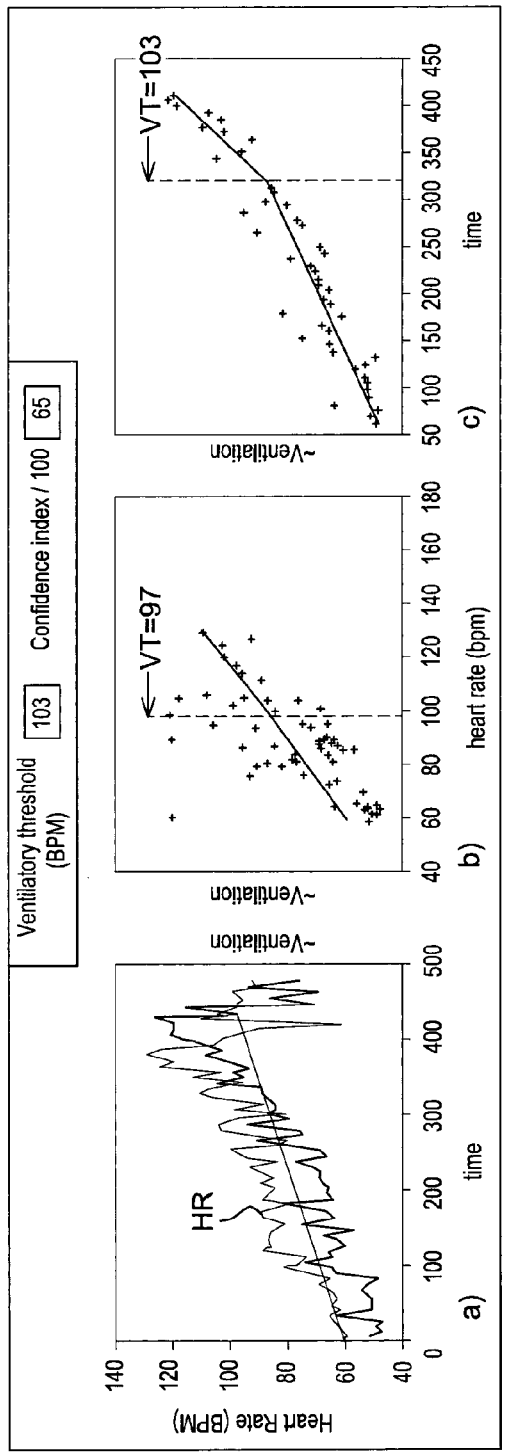

Example 3—FIG. 9

The data were acquired from an untrained, sedentary person. Due to a problem with the electrocardiogram, the heart rate values were unreliable.

The $VT_1$ could therefore not be trusted and did not match with the statistical VT3 value.

As can be seen however, branch 2 finds a good threshold of 103 with a confidence index of 65%, which is displayed to the user as selected value.

Figure 10:
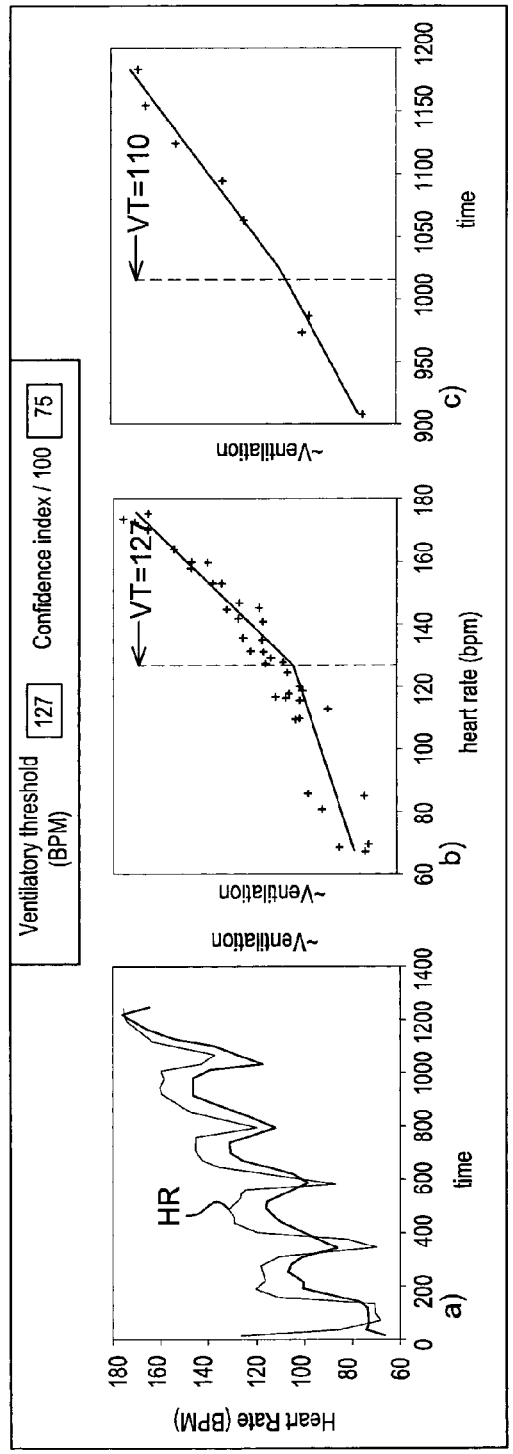

Example 4—FIG. 10

Finally, FIG. 10 reflects the situation of an untrained person under uneven effort. Due to the irregularity in the effort, not many data are available for branch 2 and the $VT_2$ of 110 has a low confidence index.

In this case, the Ventilation vs. HR also suffers from the irregularities, but more points are available. Also, the $VT_1$ value did match with the VT3 values, leading to a good confidence index.

The finally displayed values are thus those of branch 1: VT=127 with a confidence index of 75%.

The invention claimed is:

1. A method of determining a ventilatory threshold (VT) of a subject during an exercise session, said method comprising the steps of:

acquiring data relating to physiological parameters of said subject and storing said data as a function of time during said exercise session, said data including at least data acquired from a respiration sensor configured to monitor parameters relating to the respiration of said subject during said exercise session, and from a sensor configured to extract parameters relating to the heart beat pulses and/or heart beat rate of said subject during said exercise session;

executing a VT determination routine at periodic time intervals during said exercise session to detect a ventilatory threshold, the routine comprising the steps of:
  a) computing a first value of ventilatory threshold according to a first approach based on data relating to at least one of the physiological parameters acquired for said exercise session;
  b) computing a second value of ventilatory threshold according to a different, second approach based on data relating to at least one of the physiological parameters acquired for said exercise session;
  c) determining a confidence index for each of said first and second values of ventilatory threshold, wherein said confidence index reflects at least one of the detectability of the ventilatory threshold, and the matching between the value of ventilatory threshold according to one approach and that according to the other approach;
  wherein the confidence index for said first approach and/or second approach further depends on a matching with earlier calculated values of ventilatory threshold according to the same approach for the same exercise session; and
  (d) selecting one of the values of ventilatory threshold as a most reliable ventilatory threshold based on its respective confidence index.

2. The method according to claim 1, wherein said step of executing said VT determination routine is performed at periodic time intervals during said exercise session so as to provide a real-time determination of the VT during the exercise session.

3. The method according to claim 2, wherein for each iteration of said VT determination routine, the value of ventilatory threshold having the greatest confidence index is retained.

4. The method according to claim 3, wherein said retained value of ventilatory threshold is displayed with the corresponding confidence index, said value of ventilatory threshold being expressed as a time and/or heart beat rate.

5. The method according to claim 1, wherein said matching between two approaches is assessed based on the ratio:

$$\frac{VTi - VTo}{VTi}$$

where $VTi$ is the ventilatory threshold according to the current approach, and $VTo$ is the ventilatory threshold according to the other approach.

6. The method according to claim 1, wherein said matching with earlier calculated values of ventilatory threshold according to the same approach for the same exercise session is determined based on the formula:

$$\frac{1}{n-1}\sum_{i=1}^{n-1} \alpha_i |VT_n - VT_i|$$

where $VTn$ is the value determined during the current iteration of the VT determination routine and $VTi$ represents the (n−1) VT values determined earlier during the exercise session and $\alpha_i$ is a coefficient related to the corresponding confidence index.

7. The method according to claim 1, wherein the confidence index for said first approach and/or second approach further depends one or more of:
  the number of available data for calculation in each approach;
  the sum of residuals and the dispersion of the data after filtering;
  the probability of perturbation due to a warm-up threshold;
  the matching with statistical data of ventilatory threshold.

8. The method according to claim 1, wherein said first ventilatory threshold ($VT_1$) is determined, according to said first approach, from data representative of ventilation vs. heart beat rate, as the breakpoint at which ventilation starts increasing more rapidly.

9. The method according to claim 1, wherein said second ventilatory threshold ($VT_2$) is determined, according to said second approach, from data representative of ventilation vs. time, as the breakpoint at which the ventilation starts increasing more rapidly.

10. The method according to claim 1, wherein said ventilatory threshold is determined as a breakpoint at the intersection of an aerobic line with an anaerobic line fitting the data; and said detectability of the ventilation threshold is based on the ratio of the slope of the anaerobic line over the slope of the aerobic line.

11. The method according to claim 1, wherein said respiration data reflect the breathing volume and frequency of the subject as measured by a respiration sensor worn by the subject.

12. The method according to claim 11, wherein said respiration sensor comprises a chest sensor comprising an elongation sensor integrated in an expandable belt encircling the subject's chest;
  and an abdominal sensor comprising an elongation sensor integrated in an expandable belt encircling the upper abdominal region of the subject.

13. The method according to claim 12, wherein the breathing volume is estimated on the basis of the sum of the peak to valley amplitudes of the chest and abdominal sensor signals.

14. The method according to claim 1, wherein the ventilation vs. time data are processed in order to eliminate data corresponding to possible recovery and stable periods of the exercise session and keep growing trends; and the second ventilatory threshold ($VT_2$) is determined from the resulting data representing the incremental effort best fitting the whole exercise, as the breakpoint at which the ventilation starts increasing more rapidly.

15. The method according to claim 1, wherein, in accordance with a third approach, a third ventilatory threshold ($VT_3$) is determined based on statistical data; and a corresponding confidence index is determined.

16. The method according to claim 15, wherein the determination of said third ventilatory threshold ($VT_3$) further takes into account previous values of ventilatory threshold for the subject determined in prior exercise sessions.

17. The method according to claim 15, wherein the confidence index of said first and second approaches reflect the matching with said third ventilatory threshold ($VT_3$).

18. The method according to claim 15, wherein a final ventilatory threshold is determined as the ventilatory threshold with the greater confidence index.

19. A system for determining the ventilatory threshold of a subject comprising:

sensors for measuring, during an exercise session, physiological parameters of the subject to obtain at least data indicative of respiration and heart beat rate;
a memory for storing said data indicative of respiration and heart beat rate as a function of time;
a control unit configured to implement the method as claimed in claim 1.

20. The system according to claim 19, wherein said respiration parameters reflect the breathing volume and frequency of the subject as measured by the respiration sensor worn by the subject.

21. The system according to claim 20, comprising a heart rate sensor with at least a pair of ECG electrodes to be, in use, appropriately located on the subject's chest.

22. The system according to claim 20, comprising a display for displaying the retained ventilatory threshold value as an indication of time and/or heart beat rate and with the corresponding confidence index.

23. The system according to claim 20, wherein the control unit takes the form of a self-contained portable device with a battery, a command interface and a sensor interface for a wired or wireless connection.

24. Computer program product comprising instructions for causing a processor to carry out the method as claimed in claim 1 when executed in a processor unit.

25. The method according to claim 1, wherein a final ventilatory threshold is determined as the ventilatory threshold with the greater confidence index.

26. The method according to claim 18, wherein in case of equality, priority is defined by a ranking number pre-defined for each approach, and wherein the first approach has priority over the second approach, which has priority over the third approach.

* * * * *